US00PP11541P

United States Patent [19]

Olesen et al.

[11] Patent Number: Plant 11,541

[45] Date of Patent: Oct. 3, 2000

[54] MINIATURE ROSE PLANT NAMED 'POULYPSO'

[75] Inventors: L. Pernille Olesen; Mogens N. Olesen, both of Fredensborg, Denmark

[73] Assignee: Poulsen Roser ApS, Fredensborg, Denmark

[21] Appl. No.: 09/138,034

[22] Filed: Aug. 18, 1998

[51] Int. Cl.[7] ..... A01H 5/00

[52] U.S. Cl. ..... Plt./122

[58] Field of Search ..... Plt./122, 129

[56] References Cited

U.S. PATENT DOCUMENTS

P.P. 8,012 10/1992 Olesen et al. ..... Plt./122

*Primary Examiner*—Howard J. Locker

[57] ABSTRACT

A new miniature pot rose plant which has abundant, non-fading, dark red flowers and attractive foliage. The variety successfully propagates from softwood cuttings and is suitable for year round production in commercial glasshouses. This new and distinct variety has shown to be uniform and stable in the resulting generations from asexual propagation.

1 Drawing Sheet

SUMMARY OF THE INVENTION

The present invention constitutes a new and distinct variety of miniature rose plant which originated from a controlled crossing between an unnamed seedling and 'POULscal'. The two parents were crossed and the resulting seeds were planted in a controlled environment. The new variety is named 'POULypso'.

The new rose may be distinguished from its seed parent, an unnamed seedling by the same inventors, by the following combination of characteristics:

1. The unnamed seedling has orange-red flowers, whereas 'POULypso' has clear red flowers.

2. The unnamed seedling is from a crossing of a bright red floribunda 'Dalli Dalli' and 'POULvic', U.S. Plant Pat. No. 8,012 dated 27 Oct., 1992 a pink-red miniature.

The new variety may be distinguished from its pollen parent, 'POULscal' created by the same inventors, by the following combination of characteristics:

1. 'POULscal' has dark red flowers, whereas the 'POULypso' has clear red flowers.

2. The flower of 'POULscal' has a cupped flower form, whereas 'POULypso' has convex-shaped flowers.

3. 'POULscal's' growth habit is more spreading.

The objective of the hybridization of this rose variety for commercial greenhouse culture was to create a new and distinct variety with unique qualities, such as:

1. Uniform and abundant flowers;

2. Vigorous and compact growth;

3. Year-round flowering under glasshouse conditions;

4. Suitability for production from softwood cuttings in pots;

5. Durable flowers and foliage which make a variety suitable for distribution in the floral industry.

As part of their rose development program, L. Pernille Olesen and Mogens N. Olesen germinated the seeds from the aforementioned hybridization and conducted evaluations on the resulting seedlings in a controlled environment in Fredensborg, Denmark.

'POULypso' was selected by the inventors as a single plant from the progeny of the hybridization in April, 1995.

Asexual reproduction of 'POULypso' by cuttings and traditional budding was first done by L. Pernille and Mogens N. Olesen in their nursery in Fredensborg, Denmark in August, 1995. This initial and other subsequent propagations conducted in controlled environments have demonstrated that the characteristics of 'POULypso' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves, stems, and a plant of 'POULypso'. Specifically illustrated in SHEET 1:

1. Stem or entire plant showing branching and the attachment of leaves, buds, and peduncles;

2. Flower bud, partially opened bud, and open bloom;

3. Flower petals, detached;

4. Sepals, receptacle, and pedicel;

5. Flowering stem as well as a bare stem exhibiting thorns;

6. Leaves.

DETAILED DESCRIPTION OF THE VARIETY

The following is a description of 'POULypso', as observed in its growth in glasshouses in Fredensborg, Denmark and Half Moon Bay, Calif. and in field nursery in Jackson County, Oreg. Color references are made using The Royal Horticultural Society (London, England) Colour Chart, 1995, except where common terms of color are used.

For a comparison, a similar existing rose variety is 'POULrouge', a patented variety by the same inventors described and illustrated in U.S. Plant Pat. No. 9,687 and filed on Nov. 12, 1996. Chart 1 details several physical characteristics of 'POULypso' and 'POULrouge'.

CHART 1

| | 'POULypso' | 'POULrouge' |
|---|---|---|
| Bud color at ¼ open | Red Group 45A | Red Group 40B |
| Upper petal surface, open bloom | Red Group 44B | Red Group 40B |
| Reverse petal surface, open bloom | Red Group 53C | Red Group 41B |

Parents: Unnamed seedling×'POULscal'.
Classification:
*Botanical.*—*Rosa hybrida.*
*Commercial.*—Miniature.

FLOWER AND FLOWER BUD

Blooming habit: Recurrent.
Flower bud:
*Size.*—Upon opening, 18 mm–20 mm in length from base of receptacle to flower tip.
*Bud form.*—Ovoid to squarish.
*Bud color.*—As sepals unfold, Red Group 46A. Red Group 45A at ¼ opening.
*Sepals.*—Medium to strong foliaceous appendages on three of the five sepals. Surfaces of other sepals are moderately pubescent.
*Peduncle.*—Surface: Smooth. Length: 35–50 mm average length. Color: Green Group 143A. Strength: Erect.
*Receptacle.*—Surface: Smooth. Shape: Broadly urn-shaped. Size: Medium. 7 mm (w)×5 mm (h). Color: Green Group 143A.
*Borne.*—Generally with 2–4 buds per flowering stem.
Flower bloom:
*Size.*—Medium for a 12.5 cm pot rose. Average diameter is 45–55 mm when open.
*Form.*—Shape of flower when viewed from the side: Upon opening, upper part: Flattened convex. Upon opening, lower part: Convex. Open flower, upper part: Flattened convex. Open flower, lower part: Flattened convex.
*Petalage.*—Double. Average range: 35–45 under normal conditions. Reproductive organs exhibited on fully open blooms.
*Color.*—Upon opening, upper surface of the petals is Red Group 44A. Upon opening, the reverse surface is Red Group 53B. After opening, the upper surface is Red Group 44B. After opening, the reverse surface is Red Group 53C. Upon opening, a very small petal spot, White Group 155B exists on the inner and outer sides of the bases of the petals. The white color of the spot transitions to Purple Group 76D before becoming the red of petal.
*General tonality.*—No change in the general tonality at the end of the third day. At the end of the fifth day, there is a slight change to Red Group 44B to 44C.
Petals:
*Petal reflex.*—Petals reflex backwards. On exterior flowers, petals double reflexed to form point.
*Petal edge.*—Uniform and smooth.
*Petaloids.*—Commonly none.
*Fragrance.*—Light.
*Duration.*—As a pot plant, flowers last from 12 to 15 days. As a cut flower 7 to 9 days.
*Texture.*—Thick.
*Shape.*—Round.
*Form.*—Reflexed.
*Arrangement.*—Imbricated.

Reproductive organs:
*Pollen.*—Color: Orange Group 24A. Abundance: Average.
*Anthers.*—Size: Medium to large. Early Color: Greyed-Orange Group 168B with intonations of Greyed-Red Group 182C. Late Color: Greyed-Red Group 183C. Abundance: Above average.
*Filaments.*—Color: White Group 155C.
*Stigmas.*—Superior in location to anthers. Color: Green-White Group 157C to Red-Purple Group 69D.
*Styles.*—Color: Red-Purple Group 59B.

PLANT

Plant growth: Vigorous, compact, upright to bushy. When grown as a 13 cm pot plant, the average height of the plant itself is 22 to 26 cm and the average width is 22 cm.
Stems:
*Color.*—Young wood: Green Group 137B. Older wood: Green Group 137B.
*Thorns.*—Incidence: Moderate. Size: Average length: 2 mm–3 mm. Color: Variable. Red Color Group 54D to 54C with translucent areas of Green-White 157B. Shape: Slightly curved downwards.
*Bark.*—Young wood: Smooth. Older wood: Smooth.
Plant foliage: Normal number of leaflets on normal leaves in middle of the stem: 5 leaflets.
*Leaf size.*—Medium. 70–75 mm (l)×55–60 mm (w).
*Abundance.*—Average.
*Color.*—Upper Leaf Surface: Between Green Group 137A and 139A. Lower Leaf Surface: Green Group 138A. Juvenile foliage: The upper leaf surface is Green Group 147A and the lower leaf surface is Green Group 138A. Juvenile foliage has intonations of Greyed-Red Group 178A in the leaf veins, midribs, leaf undersides, and the underside margins.
Plant leaves and leaflets:
*Stipules.*—Present. Size: 7 mm–10 mm. Color: Green Group 137A. Presence of hairs: Limited marginal hairs present.
*Petiole.*—Length 15 mm–25 mm. Color: Green Group 143A. Upper surface with intonations of Greyed-Red Group 180A. Underneath: With limited prickles.
*Rachis.*—Color: Green Group 143A with intonation on upper surface of Greyed-Red Group 180A. Prickles: With prickles underneath. Upper margin with hairs.
*Leaflet edge.*—Serrated.
*Shape.*—Leaflets are: ovate.
*Other.*—Slightly glossy. Thick texture.
Disease resistance: Above Average resistance to mildew and Botrytis under normal growing conditions in Half Moon Bay, Calif. and Fredensborg, Denmark.

We claim:

1. A new and distinct variety of rose plant of the miniature class, substantially as herein illustrated and described as a distinct and novel rose variety due to its abundant, dark red flowers, vigorous and compact growth, year round flowering under glasshouse conditions, suitability for production from softwood cuttings in pots, and durable flowers and foliage which make the variety suitable for distribution in the floral industry.

* * * * *

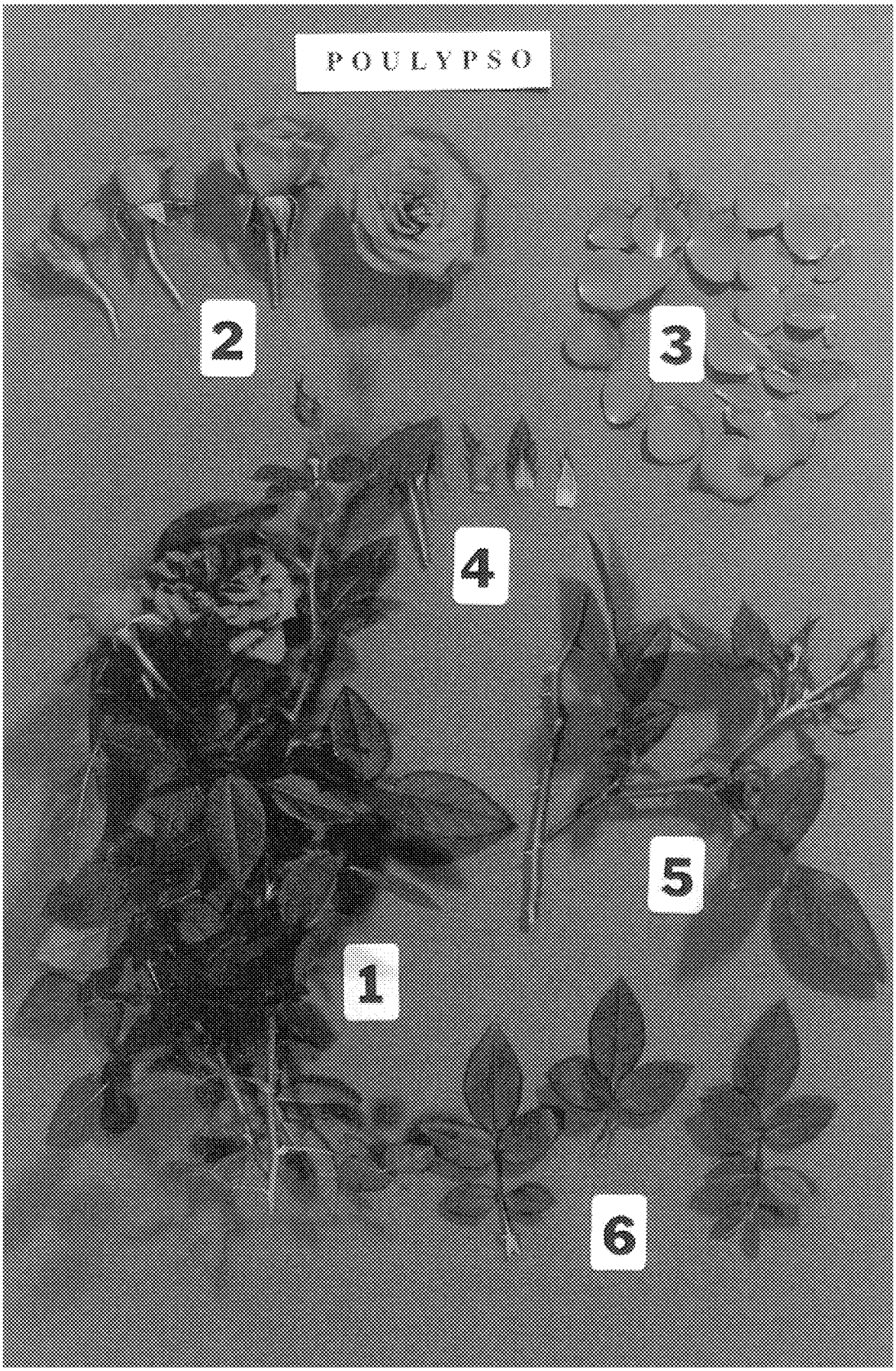
POULYPSO
2
3
4
5
1
6